(12) United States Patent
Clarke

(10) Patent No.: US 11,129,865 B2
(45) Date of Patent: Sep. 28, 2021

(54) NEUPANEX®: NEUROPROTECTIVE, NEUROREGENERATIONAL, AND NEUROGENESIS SUPPORTING SUPPLEMENT COMBINATION

(71) Applicant: Lewis Kilman Clarke, Friendswood, TX (US)

(72) Inventor: Lewis Kilman Clarke, Friendswood, TX (US)

( * ) Notice: Subject to any disclaimer, the term of this patent is extended or adjusted under 35 U.S.C. 154(b) by 0 days.

(21) Appl. No.: 16/647,494

(22) PCT Filed: Sep. 14, 2018

(86) PCT No.: PCT/US2018/051246
§ 371 (c)(1),
(2) Date: Mar. 14, 2020

(87) PCT Pub. No.: WO2019/074617
PCT Pub. Date: Apr. 18, 2019

(65) Prior Publication Data
US 2020/0268825 A1    Aug. 27, 2020

Related U.S. Application Data

(60) Provisional application No. 62/558,641, filed on Sep. 14, 2017.

(51) Int. Cl.
| | | |
|---|---|---|
| *A61K 31/00* | (2006.01) | |
| *A61K 36/899* | (2006.01) | |
| *A23L 33/105* | (2016.01) | |
| *A23L 27/30* | (2016.01) | |
| *A23L 33/155* | (2016.01) | |
| *A61K 31/05* | (2006.01) | |
| *A61K 31/07* | (2006.01) | |
| *A61K 31/12* | (2006.01) | |
| *A61K 31/122* | (2006.01) | |
| *A61K 31/197* | (2006.01) | |
| *A61K 31/221* | (2006.01) | |
| *A61K 31/375* | (2006.01) | |
| *A61K 31/385* | (2006.01) | |
| *A61K 31/4045* | (2006.01) | |
| *A61K 31/4402* | (2006.01) | |
| *A61K 31/4745* | (2006.01) | |
| *A61K 31/519* | (2006.01) | |
| *A61K 31/568* | (2006.01) | |
| *A61K 31/573* | (2006.01) | |
| *A61K 31/575* | (2006.01) | |
| *A61K 31/593* | (2006.01) | |
| *A61K 31/685* | (2006.01) | |
| *A61K 31/714* | (2006.01) | |
| *A61K 33/30* | (2006.01) | |

(52) U.S. Cl.
CPC ............ *A61K 36/899* (2013.01); *A23L 27/36* (2016.08); *A23L 33/105* (2016.08); *A23L 33/155* (2016.08); *A61K 31/05* (2013.01); *A61K 31/07* (2013.01); *A61K 31/12* (2013.01); *A61K 31/122* (2013.01); *A61K 31/197* (2013.01); *A61K 31/221* (2013.01); *A61K 31/375* (2013.01); *A61K 31/385* (2013.01); *A61K 31/4045* (2013.01); *A61K 31/4402* (2013.01); *A61K 31/4745* (2013.01); *A61K 31/519* (2013.01); *A61K 31/568* (2013.01); *A61K 31/573* (2013.01); *A61K 31/575* (2013.01); *A61K 31/593* (2013.01); *A61K 31/685* (2013.01); *A61K 31/714* (2013.01); *A61K 33/30* (2013.01); *A23V 2002/00* (2013.01)

(58) Field of Classification Search
CPC ..................................................... A61K 31/00
See application file for complete search history.

(56) References Cited

U.S. PATENT DOCUMENTS

2016/0367676 A1 *  12/2016  Burnam .................. A61K 8/31

* cited by examiner

*Primary Examiner* — Rosanne Kosson
(74) *Attorney, Agent, or Firm* — Kearney, McWilliams & Davis, PLLC; William Yarbrough

(57) ABSTRACT

The present invention provides a dietary supplement that contains necessary ingredients for neurological protection and neurogenesis in one formulation. This dietary supplement comprises combinations of vitamins and substances that are naturally endogenous to the brain, are known to decline with age, injury and disease and are essential for membrane structure, mitochondrial respiration and stem cell differentiation.

29 Claims, 1 Drawing Sheet

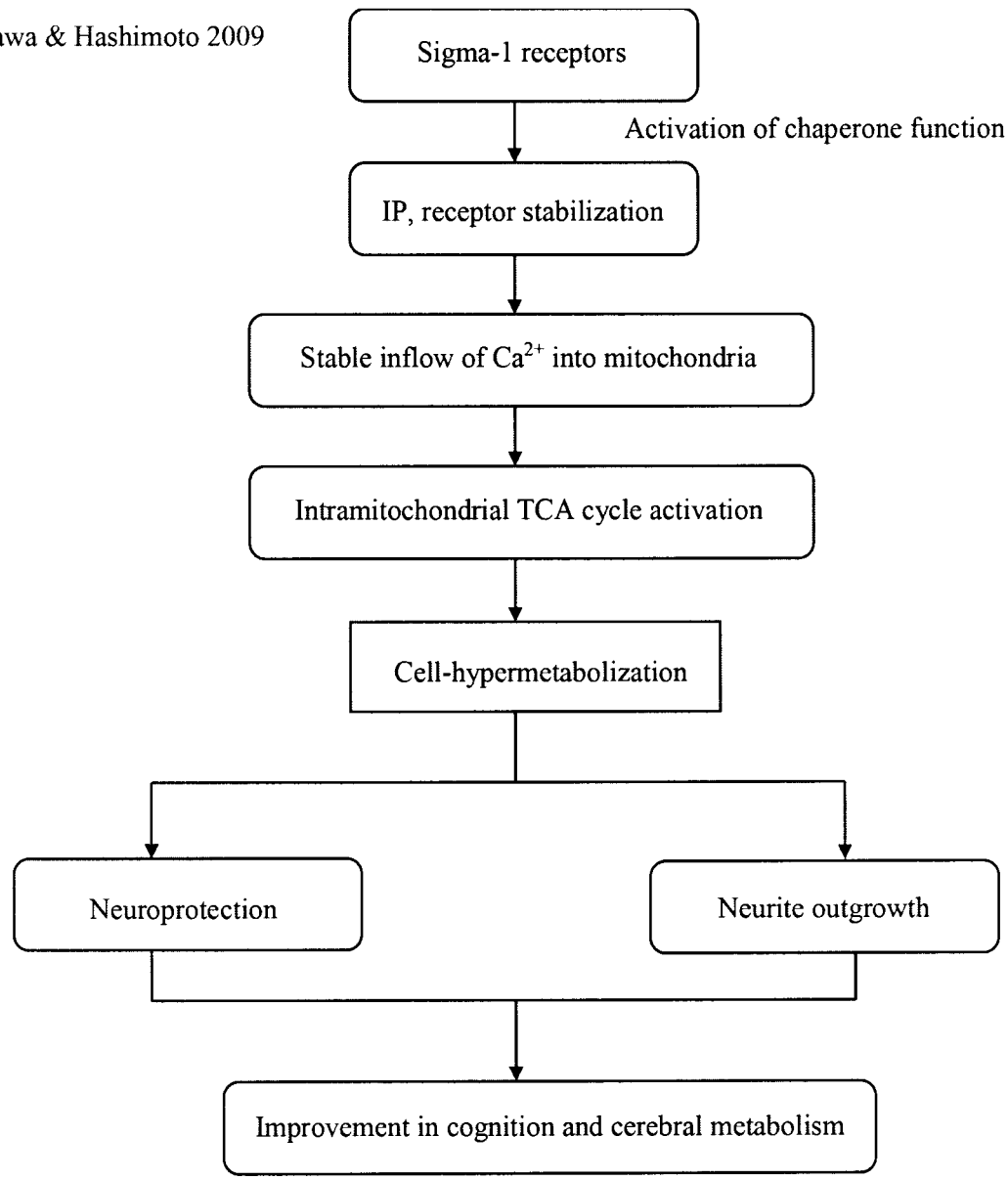

NEUPANEX®: NEUROPROTECTIVE, NEUROREGENERATIONAL, AND NEUROGENESIS SUPPORTING SUPPLEMENT COMBINATION

CROSS-REFERENCE TO RELATED APPLICATIONS

This is a U.S. National Stage under 35 USC 371 of International Patent Application No. PCT/US2018/051246 filed Sep. 14, 2018, which claims priority to U.S. Provisional Patent Application No. 62/558,641 filed Sep. 14, 2017.

BACKGROUND OF THE INVENTION

Field of the Invention

The present invention generally relates to formulations that can be used as a dietary supplement and in a multifactorial, interdependent therapy to treat neurological disorders, diseases, dysfunctions or injuries. More specifically, the present invention is drawn to formulations that comprise novel combinations of ingredients that can be used for neuroprotection, neuroregeneration, neurogenesis or a combination thereof. This invention marries several sciences into a parsimonious, yet comprehensive approach to the treatment of neurologic injury and disease. As there is no single supplement or drug that can repair the brain due to the complex fabric of its cell biology, biochemistry, neurophysiology, neuroimmunology, neuroendocrinology, and neuroanatomy. Therefore, the interactions of all these systems must be considered, their interdependence studied and therapies implemented accordingly, as current science would dictate. In addition, the biochemical and physiologic interdependence of the components of this invention requires that each component be administered concurrently to maximize the efficacy of the facilitation, inhibition and augmentation of one component on another. Accordingly, the uniqueness of this invention derives from the hitherto unrecognized necessity for this integration of every aspect of the sciences to obtain restoration of neurologic function.

Background

The final frontier in medicine is the brain. However, it is difficult to comprehend the intricacies of its anatomical network, its chemistry, the neuronal and glial cell biology, the delicate balance of inhibition, facilitation and modulation, its interactions and the ultimate control with and of the rest of the body. This is further complicated by the lack of understanding of the pathology of the brain. The current literature reveals just a few of the many mechanisms such as mitochondrial oxidative phosphorylation and beta oxidation, DNA on/off switches, membrane and nuclear receptors, endoplasmic reticulum, and mitochondrial interaction, excitotoxic neurotransmitters, free radicals, and inflammatory cascades involved in neurologic injury whether it results from ischemia, trauma, both cumulative or as a single event, or a gradual degenerative process as observed in, for instance, Alzheimer's and Parkinson's diseases, ALS, and multiple sclerosis. Even within these scantly understood mechanisms, there is vast potential for delineation of strategies for neuroprotection and neuroregeneration or neurogenesis. Due to the complexity of these systems, a single intervention or drug is an unsatisfactory approach and not a practical solution or reasonable strategy to affect a therapy for these, and other related, complex pathologies.

In detail, the combination and supplementation of naturally derived neuronal elements (i.e. endogenous components germane to brain chemistry that are essential for membrane structure and function, necessary for mitochondrial respiration, and vital in directing stem cell differentiation toward neurogenesis and myelogenesis), that represent the present invention, are utilized to operate in each of the following areas of (1) injury phase free radical scavenging, resulting from free radical release due to gradual or sudden injury or trauma, (2) protection of healthy cells from neurotoxins released from damaged neurons or glia, (3) suppression of the inflammatory response resulting from the injury process, (4) repair phase enhancement in cell-to-cell communication at the membrane lipid rafts, and (5) promotion of neuroprotection and neurogenesis. Equally, it must be observed that while these elements are naturally derived they nonetheless decrease with age, injury and disease. To understand the curative and preventative nature and the utility of the present invention's means of interruption and disruption of the pathways resulting in loss of cognitive function and physical ability as a result of injury or trauma to the brain, it is imperative to understand the mechanisms and the sequences of the pathologic cascades themselves in order to target specific sites where an intervention could disrupt this sequence and thereby halt a degenerative disease's progression.

BRIEF DESCRIPTION OF THE DRAWINGS

FIG. 1 depicts a flow diagram illustrating a pathway as detailed by Ishikawa and Hashimoto.

INJURY PHASE-FREE RADICALS—OVERVIEW OF THE OXIDATIVE DESTRUCTIVE SEQUENCE

Whether the initiating event is trauma, hemorrhage, or ischemia, the cells in the central nervous system follow a prescribed sequence of responses which are ultimately purposed to clean up and repair the damage. However, in much the same way as skin damage following a cut is cleaned up by the macrophages and fibroblasts with the resulting scarring repair never regaining all the structure and function of the original skin, so it is with damage to the neurons and glia. With the initial insult there is membrane damage to the neurons and glia alike as well as the membranes of the subcellular organelles. A release of intra and extracellular free radicals occurs from the resulting mitochondrial and cellular membrane leakage which further damages the mitochondria and adjacent neurons and glia. The damaged glia, or astrocytes, lose their intracellular glutamate into the extracellular space and this becomes neurotoxic to adjacent neurons via their glutamate receptors—thereby extending the neuronal destruction and adding more free radicals or reactive oxygen species (ROS) to further damage still more neurons and glia.

As this oxidation by the ROS continues, there is a peroxidation of membrane lipids with dissolution of the cell membranes and release of phospholipids. This results in increased arachidonic acid from these excess extracellular phospholipids. Arachidonic acid is the precursor for the cascade of prostaglandins and leukotrienes which then initiates the classic inflammatory immunologic response.

Activation of microglia by ROS, together with ROS, cause release of inflammatory cytokines IL-1, IL-18, IL-6, TNF-alpha, and metalloproteinases from ischemic and damaged neurons and glia, especially during reperfusion. This increases the permeability of the blood-brain barrier and allows infiltration by peripheral leukocytes. The surge of pro-inflammatory cytokines attracts more inflammatory cells to clean up the tissue lesions. In addition, both the activation of the microglia and the influx of the peripheral leukocytes results in production of inducible nitric oxide synthase (iNOS) which in turn produces more ROS thus perpetuating the entire sequence and extending the damage to wider and wider volume.

Therefore, within this sequence, there are several points wherein the cascade might be interrupted thus providing therapeutic interventions. One such area is the aggressive scavenging of free radical oxygen species as they exist as a reactive oxygen species (ROS) as a result of cellular damage due to brain trauma or injury (where free radicals are molecules, atoms or groups of atoms with an unpaired electron in its outer orbital) as discussed below.

Briefly, Free radicals resulting from cellular damage such as brain injury are a primarily reactive oxygen species (ROS). These are the superoxide $O2^-$ and the hydroxyl $OH^-$. Of the two, the $OH^-$ is the more toxic and reactive. These free radicals are produced in brain injury and ischemia when transition metals present in the cerebrospinal fluid catalyze the reaction of $H_2O_2$ with the superoxide $O2^-$. resulting in the $OH^-$. The most common metal involved in these reactions is iron (Fe) because there is little Fe-binding protein in the cerebrospinal fluid and Fe released from damaged cells readily donates electrons to $H_2O_2$ resulting in the free radical $OH^-$.

In normal cellular metabolism, small amounts of free radicals are produced by many processes. Auto-oxidation of catecholamines and other small molecules results in free radical production. Mitochondrial electron transport normally converts $O_2$ to $H_2O$ and avoids ROS altogether. In pathologic states, however, wherein a damaged mitochondrial membrane leaks, there can be single electron binding to $O_2$ which produces $O_2^-$. Once these ROSs are produced, they self-propagate by binding to still more molecules and this continues until they either unite with another free radical, and the two electrons form a stable bond, or intrinsic cellular defenses scavenge the lone electron.

As stated above, ROS from injured cellular membranes in the brain will react with proteins, especially sulfated amino acids, DNA and RNA, and membrane lipids with polyunsaturated fatty acids being most vulnerable because of their abundant double carbon bonds. This results in not only the destruction of progressively more and more membranes, but also a compromise in the cell's ability to function as it now has lost its ability to synthesize protein products due to its damaged DNA and RNA.

In summary, it is clear that acute, as well as gradual, brain injury results in damaged cell membranes of both neurons and glia the result of which is the release of transition metals (e.g. Iron, Zinc, Manganese, and Copper) from inside the cells to the extracellular space where they remain unbound by proteins and promote free radical formation with oxygen and hydroxyl radicals which then interrupt more membranes by oxidizing phospholipids and proteins in the membranes. This causes leaks both in the cell membrane and the mitochondrial membranes within the cells releasing more reactive oxygen species and oxidized intramembrane proteins altering receptors for neurotransmission and innumerable other vital cell respiratory functions. With loss of electron transport in the mitochondria, the cellular energy and ability to recover and repair is compromised. Whether the injury is minor or both minor and repetitive or the result of major trauma, these processes begin within minutes of the insult and continue in a vicious cycle of self-propagation.

An early therapy targeting and scavenging free radicals is paramount to halting this progression and mitigating the possibility of developing late onset neurodegenerative disease states. Components in the present invention include multiple antioxidants which are enumerated in TABLE 1A and TABLE 1B below.

TABLE 1A

Free Radical Scavengers - Guardians
of Mitochondrial and Nuclear DNA

Pyrroloquinoline Quinone (PQQ): Suppresses Reactive Nitrogen
Species and Blocks iNOS after Myocardial and CNS Ischemic Events
Menoquinone4 (Vit K2): Abolishes ROS by Inhibiting 12-LOX AND
Completely Blocks Free Radical Accumulation and Cell Death in
Vitro, Scavenges Similar to Ubiquinone
Vitamin D: Inhibits Iron and Zinc Oxidation of Membranes
DHEA, Pregnenolone, Progesterone: All Endogenous Neurosteroids
Have Antioxidant and Antiinflammatory functions

TABLE 1B

Free Radical Scavengers - Guardians of
Mitochondrial and Nuclear DNA (cont)

Acetyl-L-Carnitine: Prevents Electron Leakage from Mitochondria
B Vitamins: Antioxidant and Antiinflammatory Post Ischemic
Event Independent of Homocysteine-lowering
Melatonin: Direct Free Radical Scavenger, Stimulates
Antioxidative Enzymes, Reduces Electron Leakage, Augments
Efficiency of Other Antioxidants.
Alpha Lipoic Acid: Actively Binds Free Radical Products of
Oxidative Phosphorylation, Regenerates E and C
Ubiquinone (CoQ10): Potent REDOX Functions, Counters
Oxidation of LDL, Regenerates E and C back to antioxidant
status The Injury Phase-Neurotoxins—the Neurotoxic Effect of Glutamic Acid Glutamic acid or glutamate normally functions as an excitatory neurotransmitter in many brain nuclei and neuronal networks. However, it is also neurotoxic when large amounts are present in the extracellular space and when bound to specific glutamate receptors on these neurons. Under normal conditions, glia, specifically astrocytes, are the repository for most of the brain glutamate. If these astrocytes are damaged, the glutamate is released into the extracellular space. The blocking of these specific glutamate receptors on healthy, yet susceptible, neurons represents another point in the destructive sequence where aggressive intervention can arrest the progression of the cascade. Protecting these neurons would result in the protection of mitochondrial membranes and maintain mitochondrial function. Ultimately, saving the mitochondria saves the cell.

When cell membranes are damaged in the event of brain injury, there is an interruption of integrity of structure as previously discussed. This loss of membrane integrity results in increased permeability to ions, specifically $K^+$. Normally, astrocytes and glia can absorb excess $K^+$, but these cells are damaged by the injury and less able to do so. This leakage of $K^+$ thus depolarizes both neurons and astrocytes. The nonspecific depolarization of the astrocytes results in release of glutamate into the extracellular space. Glutamate now becomes a neurotoxin rather than a neurotransmitter. As the $K^+$ leaks out of the cell, the membrane potential is altered. There is a reflexive activation of the $Na^+$—$K^+$ pump in an attempt to restore membrane potential.

It is mitochondrial energy from oxidative phosphorylation which fuels this pump, but the mitochondrial function is already compromised by the injury and is less and less able to maintain the energy necessary to maintain membrane potential of the cell. All cells, neurons and glia, are involved in this attempt to restore $Na^+$ and $K^+$ levels and their respective membrane potentials.

With decreased ATP production from the compromised mitochondria, there is an increasing loss of neurons and astrocytes. With the loss of astrocytes, there is more and more glutamate released into the extracellular space. With this surge of glutamate, there is further depolarization of neurons which opens $Ca^{++}$ channels causing an excessive release of $Ca^{++}$. Under normal conditions, the absorption of $Ca^{++}$ is maintained by mitochondria. However, with the injury, the $Ca^{++}$ release is excessive, and because mitochondrial function is compromised, this influx of $Ca^{++}$ exceeds that which is within the mitochondrial capacity to reuptake the excess $Ca^{++}$. This further compromises the mitochondria's absorptive ability and energy output.

ATP production continues to decline in all the cells. There is a compensatory rise in glycolysis with increased lactic acid production. This relative acidosis increases membrane permeability still more and there is more mitochondrial loss and destruction to neurons and glia. There is decreased clearing of $K^+$ and glutamate by dying astrocytes with more and more extracellular $K^+$ and glutamate. And so the cycle continues without interruption.

It is clear, therefore, from this review of cellular physiology and biochemistry that an initial intervention following any genre of brain injury must include the scavenging of free radicals by antioxidant compounds and the suppression of glutamate neurotoxicity with both competitive and noncompetitive membrane N-methyl-D-Aspartate (NMDA) receptor antagonists. It should also be understood that while the focus of this discussion refers to an acute phase of brain injury, these same pathologic sequences occur in chronic neurodegenerative disease processes, albeit much more slowly. These diseases include, but are by no means limited to Parkinson's, ALS, Multiple Sclerosis, Alzheimer's Traumatic Brain Injury and dementia in all its forms, and Cumulative Traumatic Encephalopathy.

Supplements in the present invention include compounds that bind and block glutamate and glutamate receptors as discussed in TABLE 2A and TABLE 2B below.

TABLE 2A

Suppress Neurotoxin Release or Receptor Binding

Pyrroloquinoline Quinone (PQQ): Decreases NMDA Receptor Affinity-Diminishing Excitotoxicity
Menoquinone4 (Vit K2): Protects Oligodendrocytes & Neurons from Glutamate-induced Cell Death.
Vitamin D: Reduces L-Type Voltage Sensitive $Ca^{++}$ Channels-decreasing $Ca^{++}$ influx at NMDA
DHEA: The Only Neurosteroid that Decreases NMDA excitotoxicity

TABLE 2B

Suppress Neurotoxin Release or Receptor Binding (cont)

Acetyl-L-Carnitine: Protects from Neurotoxins MPTP and MPP+
B Vitamins: All B's Reduce NMDA Excitotoxicity
Melatonin: Potent NMDA Receptor Antagonist
Alpha Lipoic Acid: Modulates REDOX Site on NMDA to Reduce Excitotoxicity
Ubiquinone (CoQ10): Inhibits NMDA Receptor-induced Cell Death The Injury Phase-Inflammation—the Inflammatory Response Any tissue injury initiates an inflammatory process which begins the cleanup of damaged tissue and also stimulates the release of growth factors to initiate and begin the repair process. The inflammatory component of an injury to the central nervous system begins within the first few minutes. In chronic degenerative diseases, it is inflammation that perpetuates the destructive processes previously outlined. So, while inflammation is a necessary antecedent to repair, it should be a controlled, self-limited process. With recurrent injury, prolonged exercise, diabetes, ethanol, smoking, and infection, the body never leaves the inflammatory preparatory phase for healing. As a result, the destructive process continues as in chronic neurodegenerative diseases. For purposes of this discussion, the focus will be on the sequences that occur in the initial acute injury, but it is understood that the same applies to the chronic phase as well.

In the acute injury such as a stroke or traumatic brain injury, the destruction and increased permeability of the membranes discussed above, due to the massive release of free radicals, results in the increased oxidation of membrane lipids with lipid peroxidation of polyunsaturated fatty acids (PUFA's) in the membranes. This, in turn, results in increased free phospholipids into the extracellular fluid from the membrane phosphatidylcholine, phosphatidylethanolamine, and phosphatidylserine to be discussed below. These phospholipids are enzymatically converted by the enzyme phospholipase to arachidonic acid, a potent inflammatory molecule. While the subsequent reactions are beyond the scope of this discussion, it should be noted that arachidonic acid is the precursor for prostaglandin synthesis and the synthesis of leukotrienes both of which initiate the immunologic inflammatory cascade.

Concurrently, the ROS, previously discussed, stimulate ischemic neurons and glia to secrete inflammatory cytokines, interleukin-1 (IL-1) released immediately in the first 15-30 minutes, tumor necrosis factor alpha (TNF-alpha) released secondarily 6-24 hours later, and interleukin-1B (IL-1B), interleukin-6 (IL-6), and metalloproteinase-9 (MMP-9) making up the resultant cytokine release. The release of these cytokines produces an increase in the permeability of the blood brain barrier (BBB) which results in the infiltration of the brain with leukocytes and macrophages whose purpose is to clean up debris. But the result of this is further destruction of neurons and glia. In addition, the cytokine surge also induces adhesion molecules ICAM1 and VCAM1—both of which also increase the permeability of the BBB.

The initial ischemia or trauma will activate microglia which are the cleanup macrophages of the brain and which stimulate the production of iNOS (inducible nitric oxide synthase) which then produces more ROS. ROS again stimulates the ischemic neurons and glia to secrete more cytokines and thus the inflammatory cascade is amplified and perpetuated.

With this complex cascade that continues as a self-perpetuating vicious, destructive circle, it is easy to understand why a patient will be admitted to the ER with mild weakness in the right arm and within 24 hours, he is unable to move his entire right side or speak. The present invention seeks to limit or contain the inflammation phase by way of several biochemical compounds that are normally produced by the body, must be simultaneously present, working together synergistically and complimentary, and which, in combination, are known to suppress and block the inflammatory cytokines as well as to prevent the activation of the enzymes that initiate the inflammation cascade. Blocking this inflammatory cascade at any point will thereby mitigate damage caused by the inflammation process and thus decrease the level and degree of untoward sequalae of the aforementioned neurodegenerative conditions and disorders.

Potent "anti-inflammatories" incorporated into the current invention are listed below in TABLE 3A and TABLE 3B.

TABLE 3A

Suppression of Pro-Inflammatories

Pyrroloquinoline Quinone (PQQ): Suppresses IL-6 and CRP
Menoquinone4 (Vit K2): Suppresses IL-6 and Genes Involved in Acute Inflammatory Response
Vitamin D: Increases IL-10 (43%), Decreases IL-6 & TNF-Alpha, Activates MKP-1 interrupting LPS Inflammation
DHEA, Pregnenolone: Activates CD55 after Contusion which Inhibits Complement Convertase that would Activate the Inflammatory Cascade
Curcumin: BLOCKS ALL INFLAMMATORY CYTOKINES!

TABLE 3B

Suppression of Pro-Inflammatories (cont)

Acetyl-L-Carnitine: Documented Antiinflammatory Role esp. in Preventing Nephrotoxicity
B Vitamins: Antiinflammatory both With and Without Homocysteine Methylation
Melatonin: Blocks TNF-alpha, IL-6, and IL-1beta
Alpha Lipoic Acid: Inhibits IL-6, Metalloproteinase-9, ICAM & VCAM, NFkB (which initiates the Inflammation Cascade)
Ubiquinone (CoQ10): Decreases LPS-induced NFkB Activation, PGE-2, IL-1, and IL-6 and proteases such as collagenase (MMP-1)

The Repair Phase-Membranes—Enhancing Cell to Cell Communication: Brain Cholesterol The initial consideration in repair of nervous system tissue focuses primarily on the rebuilding of the extensive damage to the cell membranes as discussed in the above sections. Recent findings in the structure and function of cell membranes have resulted in new insights into mechanisms of cell-cell interactions. Abnormalities of sterol metabolism in dementia have been proposed with inadequate cholesterol biosynthesis or utilization and integration into cell membranes of neurons and glia. It is clearly understood that cholesterol is a primary structural component in the brain. In addition to its essential role in structure, cholesterol is required for dendrite, axon, and synapse formation, and more interestingly in axon guidance, especially during development and repair after injury. Depletion of cholesterol results in abnormalities of neurotransmission, loss of synapse and dendrites, and loss of synaptic plasticity (Koudinov and Koudinov, 2005). These primary functions of cholesterol in the brain involve the membrane of both the cell body and the organelles such as mitochondria and endoplasmic reticulum. Therefore, a discussion of the cell membrane biology is included herewith.

Prior to the 1980's the cell membrane was thought to be a homogenous bilayer of phospholipids, glycolipids and cholesterol interspersed with transmembrane proteins. In the first decade of the 2000's it became clear that the cell membrane was much more complex than this (de Meyer and Smit 2009; Huster, et. al. 1998;). It is now believed that there are consolidations or microdomains of lipids called rafts, built on a cytoskeleton actin nanostructure floating around in the membrane. These rafts are comprised of concentrations of cholesterol, which makes up about 50% of the raft, together with sphingolipids and other phospholipids such as phosphatidylserine and phosphatidylethanolamine and phosphatidylcholine and several forms of phosphatidylinositol, as well as glycolipids, and proteins. The cholesterol content in the inter-raft membrane is only about 20% and the concentration of phospholipids and unsaturated long chain fatty acids, PUFA's, is much higher in the inter-raft membrane. This arrangement results in a less viscous inter-raft membrane allowing the more viscous raft to be mobile within it. The greater the concentration of unsaturated long chain fatty acids, the greater the fluidity of the membrane. The greater the concentration of cholesterol, the more viscous will be the raft. It is at these lipid, cholesterol-rich, microdomains or rafts where cell-cell communication and neurotransmission occur. When there exists deficient rafts, which lack adequate cholesterol and inter-raft membranes with inadequate phospholipids and unsaturated fatty acids, these abnormal membranes may be responsible for neurologic deficit disorders.

An example of this is in the Smith-Lemli-Opitz Syndrome (SLOS) a congenital syndrome that symptomatically bears close resemblance to autism, whose etiology has been found to be at least in part due to a deficiency in the last step in cholesterol synthesis, specifically lacking the 7-dehydrocholesterol reductase enzyme. These children all have autistic-like neurologic symptoms. Tierney (2001) reports that individuals with SLOS have a high incidence of autism. They lack the ability to synthesize enough cholesterol for growth and for the synthesis of compounds derived from cholesterol such as cell membranes and steroid hormones. This also translates to a loss of signaling proteins such as 'sonic hedgehog' thereby altering cell-cell communication and growth and normal development. These authors also state "that supplementary cholesterol eliminates or ameliorates many of the feeding and growth problems of SLOS, and that the autistic behaviors of children with SLOS can be reduced or even eliminated by treatment with supplementary dietary cholesterol" (Kelley, 2000). An imbalance of GM1 ganglioside and cholesterol in the lipid rafts has been documented in autistic children and can be corrected by cholesterol supplementation as well as behaviors such as aggressive behaviors, self-injury, temper outbursts and trichotillomania, irritability, hyperactivity, physical growth, sleep and social interactions (Schengrund, et. al. 2012; Aneja and Tierney 2008).

In addition, it has been shown that autistic boys have an altered lipid profile with lower HDL-C levels, but no difference in LDL levels when compared to controls (Kim et. al. 2010). This is a profound discovery, because it is believed that cholesterol can only cross the blood brain barrier via HDL. Scholtz, et. al. (2013) demonstrated in rodents that increasing dietary cholesterol resulted in dramatically increased brain cholesterol. Di Paolo and Kim (2011) have found that HDL, but neither LDL nor VLDL, can, in fact, cross the blood brain barrier. If dietary cholesterol supplementation can be transported across the blood brain barrier by HDL and neuronal and glial membrane cholesterol deficiencies can be corrected in autistic children, this may provide a starting point for redressing the abnormal neurologic symptoms both of autism and possibly acute and chronic neurologic injuries and diseases. The transport of cholesterol into the brain has been the subject of much research and the brain cholesterol content is tightly regulated with most of it originating from endogenous production. However, it is not inconceivable that there could be periods when the demand for brain membrane substrates exceeds endogenous production of these substrates, such as during the period of maximal neurologic development from birth to age 2 years and again late in life when deteriorating structure is more rapid than repair mechanisms can accommodate. Given the results of these studies dietary cholesterol supplementation could potentially correct this deficiency.

The present invention has been formulated to include dietary cholesterol. A phospholipid complex containing phosphatidylserine has also been included in the present invention formula as these are critical components for the rebuilding of the lipid rafts (discussed above) and are necessary for cell-to-cell communication. In May 2003 the Food and Drug Administration gave "qualified health claim" status to phosphatidylserine thus allowing labels to state "consumption of phosphatidylserine may reduce the risk of dementia and cognitive dysfunction in the elderly" along with the disclaimer "very limited and preliminary scientific research suggests that phosphatidylserine may reduce the risk of cognitive dysfunction in the elderly. With these supplements, fundamental substrates required for repair of brain tissue have been made available as is included in the present formulation.

The Repair Phase: The Promotion of Neurogenesis
Cholesterol and Neurogenesis

Cholesterol and the phospholipids are much more than the glue of cell membranes. They are also "bioactive". Erhard Bieberich (2012), in an excellent review discusses the role of cholesterol, sphingolipids such as sphingomyelin and the ganglioside GM1, endocannabinols, steroids, lysophospholipids, and eicosanoids. These not only form the rafts that regulate the cell signaling proteins within the raft, but these lipids can also bind to a specific lipid receptor or a "kinase or phosphatase, ion exchanger, or other cell signaling protein." Most interesting is the additional discovery of lipid second messengers which regulate the energy and redox of differentiating neural stem cells. Bieberich states that "it is a cocktail of bioactive lipids and growth factors that ultimately determines the fate of differentiating stem cells." He points out that cholesterol modulates raft-associated growth factor receptor functions. And cholesterol not only functions in intercellular mechanisms and communication within the rafts, but also binds covalently to "sonic hedgehog" which is a "key mophagen in embryogenesis." Cholesterylation of "sonic hedgehog" when combined with retinoic acid, stimulates the differentiation of embryonic stems into motor neurons and, when combined additionally to fibroblast growth factor 2, cells are differentiated into the progenitors of oligodendrocytes, the parent cells of myelin.

Signal Receptors and Neurogenesis

Within the cholesterol-rich lipid rafts are signal receptors tightly associated with cholesterol and specific amino acids. Martin et. al. in 1976 identified a receptor originally thought to be an opioid receptor. It took another decade before it was learned that it was much more that this and now it is known to be involved in pain, memory, learning, mood, psychoses, neuroprotection, and neurogenesis when bound by neurosteroid ligands such as dehydroepiandrosterone (DHEA) and pregnenolone—and the list is still growing and extensively as reviewed by Maurice and Su (2009). This receptor is abundant in the mitochondrial-associated membrane lipid rafts of the endoplasmic reticulum (Hayashi and Su, 2010; Hayashi and Fujimoto, 2010). In fact, the signal receptor may actually play a role in modeling and remodeling the lipid rafts. Palmer et. al. (2007) demonstrated this remodeling of the rafts by the direct binding of cholesterol to the receptor in breast cancer cells. This may also be one of the functions of the signal receptor in the central nervous system to maintain their own environment, their distribution and their function.

While the role of sigmal receptors in development is not yet clear, it is definitely involved in myelination by differentiating neural stem cells into oligodendrocytes and their precursors (Takebayashi, et. al, 2004; Hayashi and Su, 2004). Signal receptor stimulation increases BDNF (brain-derived neurotrophic factor) which then increases neurogenesis and neurite outgrowth. One mechanism by which sigmal receptors stimulate neurogenesis is by activation due to a decreased calcium at the endoplasmic reticulum resulting in a binding to inositol triphosphate receptor which causes calcium to flow into the mitochondria which activates the intramitochondrial TCA cycle. This puts the neuron in a hypermetabolic state which results in neuroprotection and neurite outgrowth (Hayashi and Su, 2007). Therefore, sigmal receptors can function as regulators of ATP production in neurons (Ishikawa and Hashimoto, 2010) and promote neurogenesis (See TABLE 4 and FIG. 1 below for a brief description of Sigma 1 Chaperones and the pathway as described by Ishikawa and Hashimoto, et. al).

TABLE 4

| Sigma 1 Chaperone |
|---|
| Agonist binding INCREASES $Ca^{++}$ transfer from ER to Mitochondria, increasing energy output via the TCA cycle |
| Agonist binding INCREASES phosphotidylserine transfer from ER to Mitochondria where it is decarboxylated into Phosphotidylethanolomine. |
| This is transported back to the ER where it is converted into phosphotidylcholine which is utilized in making biological membranes. Constantly reconstituting and recomposing membrane lipids, microdomains and potentiates raft formation. |
| Regulates cholesterol transport into the mitochondria where it is converted to pregnenolone. Pregnenolone is transported back to the ER where it is converted to DHEA and Progesterone and subsequently to Allopregnanolone |
| DHEA, Pregnenolone Progesterone and Allopregnanolone are Sigma 1 agonists |

So neurogenesis, neuroprotection, balance of excitatory and inhibitory neurotransmission, mood, learning and memory, suppression of seizures and aberrant behaviors are somehow modulated by sigmal receptors—the number and concentration of which is dependent on the cholesterol levels in both the body and the brain. Sigmal receptors then serve to maintain these cholesterol levels thereby preserving their own integrity and that of the cell membranes. And neurosteroids in the brain are agonists to the sigmal receptor (See the described pathway as detailed by Ishikawa and Hashimoto in FIG. 1, herein).

Neurosteroids and Neurogenesis

Specific neurosteroids, both DHEA and pregnenolone, are sigma-1 agonists. This contribution of neuroendocrine mechanisms as catalysts of neuronal repair is relatively unknown and consequently unexploited. These neurosteroids which are derived from cholesterol, have been shown to improve memory and learning, impede neuronal apoptosis, and have an antidepressant-like action. (Fujimoto, et. al. 2012; Maurice, et. al. 2001). Progesterone, another neurosteroid, acts as a sigmal antagonist, but stimulates myelogenesis via another peripheral sigma-1 receptor function. It is interesting that excitatory (glutamate) neurotransmission in the brain is curtailed or inhibited by neurosteroid agonists DHEA and pregnenolone binding to the sigmal receptors. All of these findings are reviewed in the Maurice and Su 2009 paper referenced above.

DHEA, pregnenolone (and also progesterone) are all generated in the brain de novo from brain cholesterol. In syndromes with low brain cholesterol such as autism, the levels of the endogenous neurosteroids are low. A review paper by Lee and Tierney (2011) also hypothesizes the abnormal cholesterol metabolism as a fundamental etiology of autism spectrum disorders. Similarly, it could be hypothesized that other degenerative brain disorders are also the result of low levels of neurosteroids due to low brain cholesterol levels. These authors also agree that the low cholesterol results in deficiencies of neurosteroids and propose that therapeutic targets for autism should include neurosteroids and cholesterol and/or their precursors. Interestingly, while the classic steroid hormone endocrine effects are known to occur within hours to days, the latency of effects exerted by central neurosteroids on behavior can be seconds to minutes.

It must be noted that, while neurosteroids DHEA and Pregnenolone (Allopregnanolone) (See TABLE 6 and TABLES 7A and 7B below) have great potential as a supplement to endogenous neurosteroids, their inclusion into products utilized by competitive athletes is generally unadvisable as this formulation would run afoul of the United States Anti-Doping Agency vis-à-vis the World Anti-Doping Code as promulgated by the World Anti-Doping Agency (WADA). Therefore, these neurosteroids may be concertedly absent from products targeted to, designed for, and consumed by competitive athletes.

TABLE 6

| Allopregnenolone | |
| --- | --- |
| Increases Mitochondrial ATP and OxPhos Via GABAa Receptors (nongenomic) | |
| | Neurite formation |
| Promotes neurogenesis and oligodendrogenesis and white matter formation | Spatial Cognitive Performance |
| | Regulates regeneration and repair |
| Decreases neuroinflammation and Beta Amyloid in Alz Ligand for Sigma 1 and increases neurite formation | |

TABLE 7A

| DHEA |
| --- |
| Neurotransmitter |
|   Modulates GABA A |
|   Blocks NMDA Receptor |
|   Prevents Extension of CVA and Spinal Cord Injury |
| Anti-inflammatory |
|   Inhibits IL-6 & TNF Alpha |
| Antithrombotic |
| Restores FA Content of Cell Membrane |
| Restores Normal NaK-ATPase Activity |

TABLE 7B

| DHEA (cont.) | |
| --- | --- |
| Decreases Neuron Death in Ischemia-Reperfusion Hippocampal Neurotransmitter in Learning and Memory | Increases Mitochondrial Energy Metabolism Anxiolytic and Antiaggressive Binds Sigma 1 |

TABLE 7B-continued

| DHEA (cont.) | |
| --- | --- |
| Blocks Neurotoxic Effects of Cortisone | Increase Neuronal Survival |
| Prevents Scarring of Brain by Astroglia | Neurite Growth |
| Synthesized in Glial Cells | Directs Stem Cells to Neurogenesis, esp in Hippocampus |

Zinc and Neurogenesis

Decreased levels of zinc impede neurogenesis and alter lipid metabolism in the brain which in turn alters the number and the quality of lipid rafts in the cell membrane thereby decreasing the number of Sigmal receptors which then decreases both neurogenesis and neurotransmission and cell-to-cell communication and thereby decreases synthesis of the inhibitory neurotransmitter GABA. GABA inhibits excitatory neurotransmission of Glutamate. Therefore, if GABA synthesis is decreased, there is less inhibition of glutamate excitatory neurotransmission. Glutamate was previously discussed.

The present invention contains the supplement Zinc Picolinate for enhancement of neurogenesis, cell-to-cell communication and GABA synthesis.

Succinctly, with the initial insult, there is membrane damage to the neurons and glia alike as well as to the membranes of the subcellular organelles. A release of intra and extracellular free radicals occurs from the resulting mitochondrial and cellular membrane leakage, which further damages the mitochondria and adjacent neurons and glia. The damaged glia or astrocytes lose their intracellular glutamate into extracellular space and this becomes neurotoxic to adjacent neurons via their glutamate receptors. This extends the neuronal destruction and adds more free radicals or reactive oxygen species (ROS) to further damage more neurons and glia. As the oxidation by the ROS continues, there is a peroxidation of membrane lipids with the dissolution of the cell membranes and release of phospholipids. This results in the increased arachidonic acid from these excess extracellular phospholipids. Arachidonic acid is the precursor for the cascade of prostaglandins and leukotrienes, which then initiates the classic inflammatory response. Activation of microglia by ROS combined with ROS cause release of inflammatory cytokines including but not limited to IL-1, IL-1β, IL-6, and TNF-alpha and metalloproteinases from ischemic and damaged neurons and glia, especially during reperfusion. This increases the permeability of the blood brain barrier and allows infiltration by the peripheral leukocytes. The surge of pro-inflammatory cytokines attracts more inflammatory cells to clean up the tissue lesions. In addition, both the activation of the microglia and the influx of the peripheral leukocytes results in the production of inducible nitric oxide synthase (iNOS), which in turn produces more ROS. This perpetuates the entire sequence and extends the damage to wider and wider volume. Therefore, as is evidenced by the present invention, two primary determinatives can be synthesized from the above in light of current understanding: (1) the injury sets into motion multiple closely intertwined (progressively destructive) processes—each of which requiring individualized interventions—there is no single drug or supplement that will effectively arrest the cascade and progression once brain injury or trauma occurs, (2) there are points at which neuropharmacologic interventions can break the cycles and mitigate further damage to the structure of the brain and prevent devastating loss of functions such as paralysis and cognitive decline and (3) a heterogenous admixture of biochemical compounds and cumulative approach must be utilized to stop each of these destructive sequences both separately and concurrently. The present invention is designed to address all 3 of these factors discretely, contemporaneously and collectively.

As previously stated, each of the components in this invention must be included in the formulation and taken together. Cholesterol must be present with phosphatidyl serine and the other phospholipids to repair and generate membranes. Cholesterol must be augmented so that neurosteroids can be generated. Phosphatidyl serine and the other phospholipids must be present together to make the membrane Sigma 1 receptor for the neurosteroids DHEA and pregnenolone to bind, resulting in neurogenesis. The emergent scavenging of free radicals and the preserving and augmentation of mitochondrial function must include melatonin, ubiquinone, alpha lipoic acid, acetyl carnitine, vitamin K2 simultaneously. Ubiquinone, alpha lipoic acid, acetyl carnitine, K2, vitamin D, PQQ, melatonin and zinc must all be present to generate new mitochondria (mitochondrial biogenesis) and increase the number of Sigma 1 receptors and stimulate production of brain derived nerve growth factor (BDNF). Each of these, together with PQQ and vitamin D and neurosteroids must also be present to block the cytokine and interleukin inflammatory response at all its sites of initiation and propagation. Vitamin A, K2 and D must be simultaneously present together to form a heterodimer which binds to the DNA in the nucleus of cells and initiates mRNA coding and cellular function and repair. Vitamin D blocks $Ca^{++}$ influx to the NMDA receptor, preventing depolarization, while PQQ, DHEA, methylcobalamin and methylfolate, and alpha lipoic acid decrease glutamate excitotoxicity, and melatonin actually blocks the glutamate receptor.

Vitamin D

One example of this is the inextricable interactions of vitamin D in neuroprotection and neuroregeneration. In an elegant set of studies, Brewer, et. al. (The Journal of Neuroscience, 2001, 21(1):98-108) demonstrated that pretreatment with low to moderate Vitamin D concentration (10 nm-100 nm) in the hippocampal cell culture medium, but not the higher concentrations (1000 nm), had a dramatic neuroprotective effect compared to controls as measured by both electrophysiology using voltage clamp protocols as well as an infusion protocol of a toxic NMDA "insult" into the medium. This was a long-lasting neuroprotection due to the pretreatment. The mechanism of this neuroprotection appears to be due to vitamin D modulation and downregulation of the L-type low voltage Ca++ channel which has also been shown to be the mechanism of Ca++ influx contributing to excitotoxicity. The contribution of Ca++ in mitochondrial dysfunction during the injury phase has already been discussed.

There are hundreds of papers on the role of vitamin D in neuroprotection by a variety of other mechanisms. As mentioned previously, the nuclear receptor for the vitamin A and vitamin D heterodimer switches on the DNA with a resultant increased production of mRNA. Alerie Guzman de la Fuente, et. al. (2015, J. Cell Biol. Vol. 211 No. 5 975-985) and Huang, et. al. (Nat Neurosci. 2011, 14(1): 45-53) have demonstrated that when this receptor was bound by vitamin A and vitamin D, oligodendrocyte progenitor cell or stem cell differentiation into oligodendrocytes resulted. These authors propose a role for vitamin D in regeneration of demyelinating diseases such as multiple sclerosis. This can be expanded to degenerative neurologic diseases and ischemic and traumatic injuries as well.

Another example of the ubiquitous actions of vitamin D/vitamin A receptor in neuroprotection and neuroregeneration is in the regulation of the molecular chaperone heat shock proteins. These proteins are protective of cells subjected to a variety of stressors, toxic, oxidative, and ischemic, but this depends on their levels. Low levels are protective, but higher levels of these heat shock proteins increase inflammatory responses. The release of these proteins is both induced and inhibited by the heterodimer of D and A binding to the DNA nuclear receptor although the mechanism is still being researched. There is speculation that vitamin D increases the superoxide dismutase levels, thereby decreasing oxidative stress and, subsequently, the high levels of heat shock proteins back to normal lower protective levels (Calabrese, et. al., J Neurol Sci. 2005 Jun. 15; 233(1-2):145-62). "In the central nervous system, heat shock protein synthesis is induced not only after hyperthermia, but also following alterations in the intracellular redox environment. The major neurodegenerative diseases, Alzheimer's disease (AD), Parkinson's disease (PD), amyotrophic lateral sclerosis (ALS), multiple sclerosis (MS), Huntington's disease (HD) and Friedrich's Ataxia are all associated with the presence of abnormal proteins." These same authors, using the term "vitagenes" state that "manipulation of endogenous cellular defense mechanisms such as the heat shock response, through nutritional antioxidants or pharmacological compounds, represents an innovative approach to therapeutic intervention in diseases causing tissue damage, such as neurodegeneration," (Calabrese, et. al., In Vivo, 2004 May-June; 18(3):245-67).

To further demonstrate the complex interdependence of the supplements included in this invention, acetyl-L-carnitine not only provides mitochondrial energy through beta-oxidation of fatty acids, but mitochondrial protection, both direct and indirect. Calabrese, et. al. (J Neurosci Res. 2005 Feb. 15; 79(4):509-21) found that when astrocytes were treated with acetyl-L-carnitine, increased levels of heme oxygenase-1 were induced in a dose- and time-dependent manner and that this effect was associated with up-regulation of heat shock protein 60. This effect is cytoprotective particularly if vitamin D is comodulating these reactions and levels.

Closely tied to the regulatory effects of vitamins D and A on heat shock protein induced inflammation is the observed reduction in the inflammatory cytokines IL-6 and IL-1 alpha and TNF-alpha (Tukaj, et. al., Acta Biochimca Polonica, Vol. 59, No 3/2012, 395-400). It is also interesting that the lower concentrations of vitamin D were more effective than the higher concentrations. This is consistent with the hippocampal-Ca++ study discussed previously and underscores the importance of appropriate dosing of vitamin D to achieve neuroprotection as the dose-response curve is bimodal.

By extension, if the vitamin D binding proteins are reduced, there is commensurate reduction in the neuroprotective and regenerative effects of vitamin D. In this, there is an interdependence of methylfolate and methylcobalamin and the maintenance of optimal vitamin D binding protein levels. Polymorphisms of the MTHFR gene in the form of C677T mutations dramatically reduce the levels of vitamin D binding protein. These mutations have been reported to be present in as many as 50% of the population. With this mutation there is an inability to methylate folic acid which results in increased levels of homocysteine and decreased methionine and increasing both inflammatory proteins and associated diseases (Clarke, L K; Preparing the Soil: Practical Cellular Biochemistry for Regenerative Medicine, Invited Author Contributor for book chapter for J. F. S. D. Lana et al. (eds.), Platelet-Rich Plasma, Lecture Notes in Bioengineering, Springer-Verlag Berlin Heidelberg 2014) The addition to this invention of methylfolate and methylcobalamin provides the necessary methyl group supplementation to render the defective MTHFR mutation harmless and thereby decreasing the incidence of neurodegenerative diseases independent as well as interdependent with vitamin D, as per the literature. This cursory example of a single component of this invention and its complex interaction with other components of this same invention in the biochemistry, neurochemistry, neuroendrocrinology, and mitochondrial and stem cell biology represents the intellectual uniqueness of this endeavor. TABLE 8 below describes those substances important in neurogeneration.

TABLE 8

Neuroregeneration

PQQ: Increases Mitochondrial Biogenesis, Increases Nerve Growth Factor from Astrocytes (more efficient than Alpha Lipoic Acid)
Vitamin K2: Mitochondrial Electron Transport (may be better than CoQ10)
CoQ10: Mitochondrial Electron Transport and OxPhos, Mitochondrial Biogenesis,
Acetyl-L-Carnitine: Mitochondrial Fat Transport and Metabolism, Activates PGC-1 alpha-dependent mitochondrial biogenesis
Alpha Lipoic Acid: Mitochondrial Biogenesis via NO synthase-cGMP-protein kinase G pathway
Vitamin D: Increases mRNA's which encode proteins that increase mitochondrial biogenesis
Melatonin: Promotes MT 1/SIRT1/PGC-1 alpha-dependent mitochondrial biogenesis
Zinc: Augments Neurogenesis and Maintains Number of Sigma 1's by Increasing Number and Quality of Lipid Rafts.

Thus, there is a long-felt but significant and un-met need in the art for formulations that can implement a multifactorial therapy to target modification of this complex multivariate system where the formulation is positively inclusive of vitamins, minerals and elements that represent a symbiotic relationship that cannot be achieved where the disparate ingredients are taken separately (i.e. non-contemporaneously) and, thus, ineffectively. Equally, where the body is conservative and one ingredient may serve several functions and accomplish several tasks within the body (e.g. neuroregeneration, neurotoxin suppression and anti-inflammatory functions in the case of PQQ) or where phosphatidyl serine must be present with cholesterol for repair and regeneration of membranes and make Sigma-1 receptors for DHEA and pregnenolone binding, knowledge and implementation of the additive and augmented construction of the present invention exemplifies the utilization of a multi-variant solution to a manifestly complex set of conditions. The present invention satisfies this long-standing need in the art.

DESCRIPTION OF PREFERRED EMBODIMENTS

The purpose of the invention is to provide a dietary supplement and a therapy comprising the use of this dietary supplement for individuals suffering from diseases, disorders, dysfunctions or injuries including, but not limited to, Alzheimer's disease, Parkinson's disease, ALS, dementia, stroke (both hemorrhagic and ischemic), spinal cord injury, concussion, autism, multiple sclerosis, ADHD, neurodegenerative disease, Guillain-Barre syndrome, or traumatic brain injury.

The present invention discloses a dietary supplement and a multifactorial therapy method utilizing the present invention that is this dietary supplement to treat this highly complex multivariate system. Such a dietary supplement comprises all of the necessary ingredients for neurological protection and neuroregeneration in one formulation. For instance, the therapy comprising the dietary supplement described herein scavenges free radicals resulting from injuries, whether gradual or sudden, invokes protective gene expression, and protects healthy cells from neurotoxins released from damaged neurons or glia by numerous mechanisms including but not limited to blocking the release of neurotoxins and blocking the receptors for neurotoxins. Additionally, this therapy suppresses inflammatory responses resulting from the injury or process by decreasing the level of pro-inflammatory cytokines. Finally, the therapy initiates the repair process by enhancing cell to cell communication at the membrane lipid rafts, promotes neurogenesis and neurite outgrowth, and/or a combination of the above thereof.

In a preferred embodiment, the present invention provides a dietary supplement that comprises a combination of vitamins, minerals and neuroprotective and neuroregenerative substances that are naturally endogenous to the brain (yet, often resultantly deficient, unavailable, in some way stymied or simply in insufficient quantities due to disease, age or injury) which are, nonetheless essential for membrane structure, necessary for mitochondrial regeneration, and are crucial in directing stem cell differentiation toward neurogenesis and myelogenesis.

In one embodiment, the ingredients in the dietary supplement comprises a mixture of the following ingredients including but not limited to cholesterol, an acidity flavor blocker (also referred to as an acid blocker), coenzyme Q10 or CoQ10, Acetyl L-Carnitine, rice extract from rice bran (e.g. Nu-RICH)), Vitamin C, Lipoic Acid or alpha lipoic acid, sugar substitute (e.g. Stevia®), zinc picolinate, pregnenolone, folic acid or its derivative, for instance, Quatrefolic®, Vitamin B12 or methyl Vitamin B12, Pyrroloquinoline Quinone (PQQ), Vitamin D3, Vitamin K2, curcumin, phosphatidyl serine, phosphatidyl choline, phosphatidylethanolamine, phosphatidyl inositol, huperzine, gamma-aminobutyric acid (GABA) and flavor (for instance, fruit punch), or a combination thereof.

In another preferred embodiment, the ingredients in the dietary supplement comprises a mixture of the following ingredients including but not limited to cholesterol, an acidity flavor blocker (also known as an acid blocker), coenzyme Q10 or CoQ10, Acetyl L-Carnitine, rice extract from rice bran (e.g. Nu-RICER)), Vitamin C, Lipoic Acid or alpha lipoic acid, sugar substitute (e.g. Stevia®), zinc picolinate, pregnenolone, folic acid or its derivative, for instance, Quatrefolic®, Vitamin B12 or methyl Vitamin B12, Pyrroloquinoline Quinone (PQQ), Vitamin D3, Vitamin K2, curcumin, phosphatidyl serine, phosphatidyl choline, phosphatidylethanolamine, phosphatidyl inositol, huperzine, gamma-aminobutyric acid (GABA), L-carnitine and flavor (for instance, fruit punch) or a combination thereof.

In certain embodiments, the dietary supplement may comprise a derivative, an analog, an active isomer or a metabolite of these ingredients or a combination thereof. For instance, it may include cholesterol, or a derivative, an analog, or an active isomer of cholesterol or a combination thereof. It may include CoQ10, or a derivative, an analog, or an active isomer of CoQ10 or a combination thereof. It may include L-Carnitine, or a derivative of L-Carnitine including but not limited to acetyl L-Carnitine, an analog, or an active isomer of L-Carnitine or a combination thereof.

The Vitamin C in the dietary supplement may, for example, be in the form of ascorbic acid. In certain embodiments, the dietary supplement of the present invention may include a derivative of vitamin C including but not limited to one or more salts of ascorbic acid, an analog of vitamin C or a combination thereof. Examples include, but are not limited to calcium ascorbate, sodium ascorbate, and other mineral ascorbates; ascorbic acid with bioflavonoids; and combination products, such as Ester-C®, which contains calcium ascorbate, dehydroascorbate, calcium threonate, xylonate, and lyxonate.

The dietary supplement may include lipoic acid, or a derivative of lipoic acid including but not limited to alpha lipoic acid, an analog, or an active isomer of lipoic acid or a combination thereof. The dietary supplement may include a sugar substitute, including but not limited to Stevia, a derivative, an analog or an active isomer of the sugar substitute or a combination thereof. It may include dehydroepiandrosterone, a derivative, an analog or an active isomer of dehydroepiandrosterone or a combination thereof. It may include picolinate, a derivative of picolinate including but not limited to zinc picolinate, an analog or an active isomer of picolinate or a combination thereof. It may include pregnenolone, or a derivative, an analog or an active isomer of pregnenolone or a combination thereof. It may include folic acid, a derivative of folic acid including but not limited to quatrefolic, an analog or an active isomer of folic acid or a combination thereof.

It may include cobalamin, a derivative of cobalamin including but not limited to methylcobalamin, adenosylcobalamin, hydroxycobalamin, an analog of cobalamin, or a combination thereof. It may include Pyrroloquinoline Quinone, a derivative, an analog or an active isomer of pyrroloquinoline quinone or a combination thereof. It may include vitamin D, or a derivative of vitamin D including but not limited to vitamin D3 or cholecalciferol, an analog or an active isomer of vitamin D3 or a combination thereof. It may include vitamin K, or a derivative of vitamin K including but not limited to menaquinone or vitamin K2, an analog or an active isomer of vitamin K or a combination thereof. It may include curcumin, or a derivative, an analog or an active isomer of curcumin or a combination thereof. It may include serine, or a derivative of serine including but not limited to phosphatidyl serine, an analog or an active isomer of serine or a combination thereof. It may include choline, or a derivative of choline including but not limited to phosphatidyl choline, an analog or an active isomer of choline or a combination thereof. It may include inositol, or a derivative of inositol including but not limited to phosphatidyl inositol, an analog or an active isomer of inositol or a combination thereof. It may include ethanolamine, or a derivative of ethanolamine including but not limited to phosphatidyl ethanolamine, an analog or an active isomer of ethanolamine or a combination thereof. Further, it may include a derivative, analog, isomer or some natural or synthetic variation of Vitamin A, huperzine, or GABA as warranted by specific requirements and functions of the above neuro-therapeutic formulation.

In another embodiment, the dietary supplement may comprise the abovementioned ingredients in the pure, substantially pure or synthetic form, as determined by any suitable method for determination of purity that is well accepted and established.

In yet another embodiment, the representative dietary supplement may comprise about 75 mg to about 4000 mg of cholesterol, about 50 mg to about 3000 mg of Fruit Punch Flavor, about 20 mg to about 5000 mg of Acidity Flavor Blocker, about 10 mg to about 5000 mg of coenzyme Q10 or CoQ10, about 10 mg to about 5000 mg of Acetyl L-Carnitine, about 10 mg to about 5000 mg of Rice Extract, about 20 mg to about 10000 mg of Vitamin C, about 15 mg to about 2000 mg of Lipoic Acid or alpha lipoic acid, about 10 mg to about 700 mg of sugar substitute, for instance, Stevia 90%, about 50 mcg to about 150 mcg of huperzine, about 1 mg to about 500 mg of zinc picolinate, about 1 mg to about 1000 mg of pregnenolone, about 150 mg to about 2000 mg of gamma-aminobutyric acid (GABA), about 0.1 mg to about 200 mg of folic acid or its derivative, for instance, Quatrefolic®, about 0.1 mg to about 200 mg of Vitamin B12 or methyl Vitamin B12, about 0.1 mg to about 200 mg of Pyrroloquinoline Quinone, about 1 mcg to about 500 mg of Vitamin D3, about 1 mcg to about 5 mg of Vitamin K2, about 2500 IU to 10,000 IU of Vitamin A, about 10 mg to about 5000 mg of curcumin, about 10 mg to about 700 mg of phosphatidyl serine, about 1 mg to about 1000 mg of phosphatidyl choline, about 0.5 mg to about 200 mg of phosphatidyl inositol, and about 1 mg to about 1000 mg of phosphatidylethanolamine.

The above preferred embodiments may or may not include DHEA (dehydroepiandrosterone), also commonly referred to as androstenolone, as an adjunct and addition to the previously described formulation as this substance, which is a steroid hormone naturally produced in the adrenal glands of the human body and is the most abundant hormone in the blood stream, it is nonetheless a prohibited substance under the World Anti-Doping Code of the World Anti-Doping Agency (WADA), which manages drug testing for Olympics and other sports. The inclusion of this ingredient is therefore unwarranted in products that would be consumed by competitive athletes. It is equally not recommended in pediatric or adolescent populations.

The above preferred embodiments may be further augmented through the inclusion of naturally occurring cannabinoids derived from the hemp plant (*Cannabis sativa*), namely cannabidiol (CBD), or one of over 100 active phytocannabinoids. CBD is a preferred, non-psychoactive compound that interacts with the endocannabinoid system, through cannabinoid receptors, to potentiate the alleviation of the symptoms of various debilitating conditions including several neurodegenerative diseases, seizure disorders, mood disorders, and muscular and inflammatory conditions and has been studied most predominantly. Specifically, CBD has gained orphan status in the United States for the treatment of Dravet's syndrome and has been approved for the treatment of Multiple Sclerosis in the United Kingdom and Sweden. Yet, as research broadens in light of further research into cannabinoids, other phytocannabinoids, or their natural or synthetic derivatives, may as well be incorporated into the above proposed formulation. Too, though, CBD is a prohibited substance under the World Anti-Doping Code of the World Anti-Doping Agency (WADA), and as such is precluded from use by competitive athletes and may be conspicuously absent from formulations geared toward consumption by athletes.

The above preferred embodiments may include an additional supplement of Curcumin. A review of the unparalleled suppression of all inflammatory cytokines by curcumin can be reviewed elsewhere. Curcumin may be included in the present invention for that purpose of inflammatory cytokine suppression with an added benefit as a potent free radical scavenger/antioxidant.

A representative formulation of the dietary supplement, shown in TABLE 9 and TABLE 10, depicts representative concentrations per packet representing a once daily dose for each of the ingredient combination examples of 2 variations of the present invention. Further TABLE 10 shows milligram strengths (per packet) and optimal ranges of each ingredient of another variation of the present invention. Although these are two examples of the ingredients in a representative, preferred formulation with the representative forms and representative dosages per serving, the present invention broadly encompasses other formulations that have variations in the types of ingredients, forms and dosages per serving. Namely, certain ingredients may be patently absent from formulations designed for and administered to competitive athletes (e.g. DHEA and *Cannabis*) and/or absent melatonin with an acknowledgement toward the high degree of sedation and its capacity to induce drowsiness.

In still yet another embodiment, the dietary supplement described herein is in a powder form that can be dissolved in water, juice or fruit sauce, where the powder may or may not be flavored. Moreover, the preparation of the formulations of the present invention is not limited to a specific manufacturing process.

In further yet another embodiment, the powder is administered by means including, but not limited to oral, buccal, sublingual, rectal, transdermal, intravenous, intramuscular, subcutaneous, or intraperitoneal. For instance, in the event that the patient is unable to swallow due to paralysis, the powder can simply be mixed with water and administered through the patient's nasogastric or gastric feeding tube (e.g. NG-tube and PEG, G-button/G-tube respectively).

In another embodiment, there is a method of treating an individual by administering this dietary supplement to the individual, where the dietary supplement provides neurological protection and regeneration by scavenging free radicals resulting from injuries whether gradual or sudden, increasing gene expression, protecting healthy cells from neurotoxins released from damaged neurons or glia by mechanisms including but not limited to blocking the release of neurotoxins, blocking the receptors for neurotoxins or a combination thereof, suppressing inflammatory responses resulting from the injury or process by decreasing the level of pro-inflammatory cytokines, enhancing cell to cell communication at the membrane lipid rafts, and promoting neurogenesis, promoting neurite outgrowth, or a combination thereof. In yet another embodiment, the inflammatory cytokines include but are not limited to IL-1, IL-1β, IL-6, and TNF-alpha.

In still yet another embodiment, the dietary supplement protects the individual from detrimental effects of concussions, regenerates the neuronal network after such injury, or a combination thereof and/or protects the individual's myocardium after ischemic reperfusion. In further yet another embodiment, the individual benefitting from the administration of this dietary supplement may be one who is suffering from Alzheimer's, Dementia, Parkinson's disease, ALS, strokes (both hemorrhagic and ischemic), spinal cord injury, concussion, autism, multiple sclerosis, ADHD, neurodegenerative disease, Guillain-Barre syndrome, or traumatic brain injury.

It is to be understood that the dietary supplement of the present invention can also be prepared and administered with any pharmaceutically acceptable carrier or carriers. Moreover, a dietary supplement of the present invention can also be prepared in such a manner that the formulation comprises one or more pharmaceutically acceptable excipients. Examples of some of the various classes or types of excipients that may be used in preparation of the dietary supplement include, but are not limited to, flavoring agents, coloring agents, stabilizing agents, binders, disintegrants, and other well-accepted types of excipients that are safe and effective for human use and consumption. Because it is well understood that the number and type of specific excipients is too exhaustive and numerous to be listed here, it is to be understood that the inventors of the present invention have contemplated that the dietary supplement of the present invention may comprise any suitable combination of one or more pharmaceutically acceptable excipients, for instance, for preparation and manufacturing of the dietary supplement. Such representative excipients that may be used for preparation of the dietary supplement (for instance, for preparation of a suitable dosage form for administration of a dietary supplement) may include, but are not limited to, one or more of the pharmaceutically acceptable excipients disclosed in the "Handbook of Pharmaceutical Excipients" (sixth edition; edited by Rowe, Sheskey and Quinn), which is herein incorporated by reference.

The foregoing descriptions of the embodiments of the present invention have been presented for purposes of illustration and description. They are not intended to be exhaustive or to limit the present invention to the precise forms disclosed. The exemplary embodiments were chosen and described in order to best explain the principles of the present invention and its practical application, to thereby enable others skilled in the art to best utilize the present invention.

TABLE 9

|  | Per Packet | 30 Packets | 60 Packets Grams | 90 Packets | 120 Packets |
|---|---|---|---|---|---|
| Cholesterol | 1.5 | 45 | 90 | 135 | 180 |
| Fruit Punch Flavor | 1.5 | 45 | 90 | 135 | 180 |
| Acid Blocker | 1 | 30 | 60 | 90 | 120 |
| CoQ-10 | 1 | 30 | 60 | 90 | 120 |
| Acetyl L-Carnitine | 1 | 30 | 60 | 90 | 120 |
| GABA | 1 | 30 | 60 | 90 | 120 |
| NuRice | 0.75 | 22.5 | 45 | 67.5 | 90 |
| Curcumin | 0.6 | 18 | 36 | 54 | 72 |
| Vitamin C | 0.5 | 15 | 30 | 45 | 60 |
| Apha Lipoic Acid | 0.4 | 12 | 24 | 36 | 48 |
| Stevia | 0.175 | 5.25 | 10.5 | 15.75 | 21 |
| DHEA | 0.025 | 0.75 | 1.5 | 2.25 | 3 |
| Zinc Piccolinate | 0.02 | 0.6 | 1.2 | 1.8 | 2.4 |
| Pregnenolone | 0.02 | 0.6 | 1.2 | 1.8 | 2.4 |
| Melatonin | 0.006 | 0.18 | 0.36 | 0.54 | 0.72 |
| Quatrefolic | 0.006 | 0.18 | 0.36 | 0.54 | 0.72 |
| Methyl B12 | 0.003 | 0.09 | 0.18 | 0.27 | 0.36 |
| Phosphatidyl Serene | 0.128 | 3.84 | 7.68 | 11.52 | 15.36 |
| PQQ | 0.02 | 0.6 | 1.2 | 1.8 | 2.4 |
| Vitamin D3 1% | 0.05 | 1.5 | 3 | 4.5 | 6 |
| Vitamin K2 2500 ppm | 0.04 | 1.2 | 2.4 | 3.6 | 4.8 |
| Total Pack Weight |  |  | 9.743 |  |  |

TABLE 10

NEUPANEX

|  | Per | 30 | 60 Grams | 90 | 120 |
|---|---|---|---|---|---|
| Cholesterol | 1.5 | 45 | 90 | 135 | 180 |
| Fruit Punch | 1.5 | 45 | 90 | 135 | 180 |
| Acid Blocker | 1 | 30 | 60 | 90 | 120 |
| CoQ-10 | 1 | 30 | 60 | 90 | 120 |
| Acetyl L-Carnitine | 1 | 30 | 60 | 90 | 120 |
| GABA | 1 | 30 | 60 | 90 | 120 |

TABLE 10-continued

NEUPANEX

| | Per | 30 | 60 | 90 | 120 |
|---|---|---|---|---|---|
| | | | Grams | | |
| NuRice | 0.75 | 22.5 | 45 | 67.5 | 90 |
| Curcumin | 0.6 | 18 | 36 | 54 | 72 |
| Vitamin C | 0.5 | 15 | 30 | 45 | 60 |
| Apha Lipoic Acid | 0.4 | 12 | 24 | 36 | 48 |
| Stevia | 0.175 | 5.25 | 10.5 | 15.75 | 21 |
| DHEA | 0.025 | 0.75 | 1.5 | 2.25 | 3 |
| Zinc Piccolinate | 0.02 | 0.6 | 1.2 | 1.8 | 2.4 |
| Pregnenolone | 0.02 | 0.6 | 1.2 | 1.8 | 2.4 |
| Melatonin | 0.006 | 0.18 | 0.36 | 0.54 | 0.72 |
| Quatrefolic | 0.006 | 0.18 | 0.36 | 0.54 | 0.72 |
| Methyl B12 | 0.003 | 0.09 | 0.18 | 0.27 | 0.36 |
| Phosphatidyl | 0.128 | 3.84 | 7.68 | 11.52 | 15.36 |
| PQQ | 0.02 | 0.6 | 1.2 | 1.8 | 2.4 |
| Vitamin D3 1% | 0.05 | 1.5 | 3 | 4.5 | 6 |
| Vitamin K2 | 0.04 | 1.2 | 2.4 | 3.6 | 4.8 |
| Total Pack Weight | | | 9.743 | | |

TABLE 11

| Ingredient | Per Packet Concentration | Range |
|---|---|---|
| Cholesterol NF | 15 g | 75 mg-4000 mg |
| Fruit Punch Flavor | 15 g | 50 mg-3000 mg |
| Acidity Flavor Blocker | 1 g | 20 mg-5000 mg |
| CoQ-10 | 1 g | 10 mg-5000 mg |
| Acetyl L-Carnitine | 1 g | 10 mg-5000 mg |
| NuRice | 750 mg | 10 mg-5000 mg |
| Vitamin C | 500 mg | 20 mg-10000 mg |
| Apha Lipoic Acid | 400 mg | 15 mg-2000 mg |
| Stevia 90% | 175 mg | 10 mg-700 mg |
| Huperizine A | 100 mcg | 50 mcg-200 mcg |
| Zinc Piccolinate | 20 mg | 1 mg-500 mg |
| Pregnenolone | 20 mg | 1 mg-1000 mg |
| GABA (gamma-aminobutyric acid) | 1000 mg | 250 mg-1500 mg |
| Methyl Folate | 6 mg | .1 mg-200 mg |
| Methyl B12 | 3 mg | .1 mg-200 mg |
| PQQ (Pyrroloquinoline quinone) | 20 mg | .1 mg-200 mg |
| Vitamin D3 | 125 mcg | 1 mcg-5 mg |
| Vitamin K2 mk4 | 3 mcg | 1 mcg-5 mg |
| Vitamin A (palmitate) | 5000 IU | 2500 IU-10,000 IU |
| Curcumin | 600 mg | 10 mg-5000 mg |
| Phosphatidyl Serene Complex | | |
| phosphatidylserine | 100 mg | 10 mg-700 mg |
| phosphatidylcholine | 25 mg | 1 mg-1000 mg |
| phosphatidylethanolamine | 2.5 mg | 1 mg-1000 mg |
| phosphatidylinositol | 1.5 mg | .5 mg-200 mg |

What I claim is:

1. A formulation for enhancing the neurological function of a human through neurological protection and regeneration by scavenging free radicals resulting from injuries, illness or age, increasing gene expression, protecting healthy cells from neurotoxins released from damaged neurons or glia by mechanisms including but not limited to blocking the release of neurotoxins, blocking the receptors for neurotoxins or a combination thereof, suppressing inflammatory responses resulting from the injury or process by decreasing the level of pro-inflammatory cytokines, enhancing cell to cell communication at the membrane lipid rafts, and promoting neurogenesis, promoting neurite outgrowth, or a combination thereof, comprising therapeutically effective amounts of:
   a. cholesterol;
   b. coenzyme Q10 (CoQ 10);
   c. acetyl L-carnitine;
   d. rice extract from rice bran;
   e. Vitamin C in the form of ascorbic acid, calcium ascorbate, sodium ascorbate, other mineral ascorbates, ascorbic acid with bioflavonoids and combinations thereof;
   f. lipoic acid or alpha-lipoic acid;
   g. zinc picolinate;
   h. pregnenolone;
   i. folic acid or methylfolate;
   j. Vitamin B12, methyl Vitamin B12, cobalamin, methylcobalamin, adenosylcobalamin, or hydroxycobalamin;
   k. Pyrroloquinoline Quinone (PQQ);
   l. Vitamin D3, cholecalciferol or ergocalciferol;
   m. Vitamin K2;
   n. Vitamin A in the form of palmitate;
   o. Curcumin;
   p. phosphatidyl serine;
   q. phosphatidyl choline;
   r. phosphatidylethanolamine;
   s. phosphatidyl inositol;
   t. gamma-aminobutyric acid (GABA); and
   u. huperzine A: and amounts effective for palatability of;
   v. an acidity flavor blocker (also referred to as an acid blocker)
   w. a sugar substitute; and
   x. a flavoring.

2. The formulation of claim 1, wherein the ingredients fall into the following ranges: cholesterol in the range of 75 mg-4000 mg, an acidity flavor blocker in the range of 20 mg to 5000 mg, flavoring 50 mg to 3000 mg, coenzyme Q10 (CoQ10) in the range of 10 mg to 5000 mg, acetyl L-carnitine in the range of 10 mg to 5000 mg, rice extract from rice bran in the range of 10 mg to 5000 mg, Vitamin C in the form of ascorbic acid, calcium ascorbate, sodium ascorbate, other mineral ascorbates, ascorbic acid with bioflavonoids and combinations thereof in the range of 20 mg to 10,000 mg, lipoic acid or alpha-lipoic acid in the range of 15 mg to 2000 mg, sugar substitute in the range of 10 mg to 700 mg, huperzine in the form of huperzine A in the range of 50 mcg to 200 mcg, zinc picolinate in the range of 1 mg to 500 mg, pregnenolone in the range of 1 mg to 1000 mg, folic acid or Methylfolate in the range of 0.1 mg to 200 mg, Vitamin B12 (methyl B12) in the range of 0.1 mg to 200 mg, Pyrroloquinoline Quinone (PQQ) in the range of 0.1 mg to 200 mg, Vitamin D3 in the range of 1 mcg to 500 mg, Vitamin K2 in the range of 1 mcg to 5 mg, Vitamin A in the form of palmitate in the range of 2500 IU to 10000 IU, curcumin in the range of 10 mg to 5000 mg, phosphatidyl serine in the range of 10 mg to 700 mg, phosphatidyl choline in the range of 1 mg to 1000 mg, phosphatidylethanolamine in the range of 1 mg to 1000 mg, phosphatidyl inositol in the range of 0.5 mg to 200 mg, and gamma-aminobutyric acid (GABA) in the range of 150 mg to 2000 mg.

3. The formulation of claim 2, wherein phosphatidyl serine, phosphatidyl choline, phosphatidyl ethanolamine, phosphatidylethanolamine, and/or phosphatidyl inositol are included alone or as a phosphatidyl serine complex.

4. The formulation of claim 2, further comprising a therapeutically effective amount of melatonin, as a neurotoxin suppressant.

5. The formulation of claim 2, further comprising a therapeutically effective amount of dehydroepiandrosterone (DHEA) and/or cannabis, and/or cannabidiol (CBD).

6. The formulation of claim 2, further comprising a therapeutically effective amount of dehydroepiandrosterone.

7. The formulation of claim 2, wherein there may be further included excipients, binders, fillers, emulsifiers, flavoring agents, disintegrants, pharmaceutically accepted carriers or the like considered generally safe for human consumption that may make the present invention suitable for oral, buccal, sublingual, rectal, transdermal, intravenous, intramuscular, subcutaneous, or intraperitoneal administration.

8. The formulation of 1, wherein the formulation protects the individual from detrimental effects of concussions, regenerates the neuronal network after such injury, or a combination thereof and/or protects the individual's myocardium after ischemic reperfusion.

9. The formulation of claim 1, wherein the individual benefitting from the administration of this formulation may be one who is suffering from Alzheimer's, Dementia, Parkinson's disease, ALS, strokes (both hemorrhagic and ischemic), spinal cord injury, concussion, autism, multiple sclerosis, ADHD, neurodegenerative disease, Guillain-Barre syndrome, or traumatic brain injury.

10. A method of protecting and enhancing the neurological function of a human via a multifactorial and comprehensive supplementation of ingredients, thereby advancing neuroprotection, neuroregeneration, neurogenesis or a combination thereof, by way of remediating neurodestructive effects by targeting 5 distinct areas, comprising administering a therapeutically effective amount of the composition of claim 1, wherein the composition of claim 1 further comprises a therapeutically effective amount of melatonin, wherein:
   a. introducing multiple antioxidants, during injury phase of both neurons and glia resulting in free radical scavenging, results in the remediating of free radical release due to gradual or sudden injury or trauma;
   b. binding and blocking glutamate and glutamate receptors protects of healthy cells from neurotoxins released from damaged neurons or glia;
   c. the inflammatory response through inclusion of natural antiinflammatories to counter the inflammatory process resulting from the injury process is suppressed;
   d. cell-to-cell communication at the membrane lipid rafts through cholesterol and phospholipids is enhanced or repaired; and
   e. neuroprotection and neurogenesis through the addition of sigma 1 agonists, Zinc and low to moderate amounts of Vitamin D is promoted.

11. The method of claim 10, wherein the composition that is administered further comprises the antioxidants dehydroegiandrosterone (DHEA), progesterone, and/or B Vitamins.

12. The method of claim 10, wherein the composition that is administered further comprises dehydroepiandrosterone (DHEA) and/or B vitamins as neurotoxin suppressors of glutamate (glutamic acid) or glutamic receptor binding.

13. The method of claim 10, wherein the composition that is administered further comprises dehydroegiandrosterone (DHEA) and/or B vitamins as suppressors of pro-inflammatory agents.

14. The method of claim 10, wherein the repair phase, cell-to-cell communication at the membrane lipid rafts and ft raft-associated growth factor receptor function is supported by the inclusion of cholesterol, phosphatidylserine, phosphatidyl-ethanolamine, phosphatidylcholine and/or phosphatidylinositol.

15. The method of claim 10, wherein the composition that is administered further comprises dehydroepiandrosterone (DHEA), progesterone and/or allopregnenalone to maintain cholesterol levels and, wherein sigma-1 agonists potentiate neurogenesis.

16. The method of claim 10, wherein the composition that is administered further comprises dehydroepiandrosterone (DHEA), and wherein the DHEA, pregnenalone, CoQ10, acetyl-l-carnitine, alpha-lipoic acid, melatonin, zinc, Vitamin D, Vitamin A and Vitamin K2 are neuroprotectants and neuroregenerators that work symbiotically.

17. The method of claim 10, wherein zinc is included for the enhancement of neurogenesis, cell-to-cell communication and GABA synthesis.

18. The method of claim 10, wherein cholesterol must be present with phosphatidyl serine and the other phospholipids to repair and generate membranes.

19. The method of claim 10, wherein phosphatidyl serine and the other phospholipids must be present together to make the membrane Sigma 1 receptor for the neurosteroids DHEA and pregnenolone to bind, resulting in neurogenesis.

20. The method of claim 10, wherein free radical scavengers must include melatonin, ubiquinone, alpha lipoic acid, acetyl carnitine, and vitamin K2 simultaneously to preserve and augment mitochondrial function.

21. The method of claim 10, wherein CoQ-10, alpha lipoic acid, acetyl carnitine, K2, vitamin D, PQQ, melatonin and zinc must all be present to generate new mitochondria (mitochondrial biogenesis) and increase the number of Sigma 1 receptors and stimulate production of brain derived nerve growth factor (BDNF).

22. The method of claim 10, wherein the composition that is administered further comprises dehydroepiandrosterone (DHEA) and neurosteroids, and wherein the PQQ, Vitamin D, DHEA, neurosteroids and pregnenalone block the cytokine-mediated and interleukin-mediated inflammatory responses.

23. The method of claim 10, wherein Vitamin A, K2 and D must be simultaneously present together to form a heterodimer which binds to the DNA in the nucleus of cells and initiates mRNA coding and cellular function and repair.

24. The method of claim 10, wherein the composition that is administered further comprises dehydroepiandrosterone (DHEA), wherein the Vitamin D blocks Ca++ influx to the NMDA receptor, thereby inhibiting depolarization, while the PQQ, DHEA, methylcobalamin, methylfolate, and alpha-lipoic acid decrease glutamate excitotoxicity.

25. The method of claim 10, wherein melatonin blocks the glutamate receptor.

26. The method of claim 10, wherein Vitamin A and Vitamin D are included together for their augmented neuroprotective capacity.

27. The method of claim 10, wherein methylfolate and methylcobalamin are included together to sustain optimal vitamin D binding protein levels.

28. The method of claim 10, wherein the method protects the individual from detrimental effects of concussions, regenerates the neuronal network after such injury, or a combination thereof and/or protects the individual's myocardium after ischemic reperfusion.

29. The method of claim 10, wherein the individual benefitting from the administration of this method may be one who is suffering from Alzheimer's, Dementia, Parkinson's disease, ALS, strokes (both hemorrhagic and ischemic), spinal cord injury, concussion, autism, multiple sclerosis, ADHD, neurodegenerative disease, Guillain-Barre syndrome, or traumatic brain injury.

* * * * *